(12) United States Patent
Kanthasamy et al.

(10) Patent No.: US 10,843,177 B2
(45) Date of Patent: Nov. 24, 2020

(54) COMPOSITION AND PROCESS THEREOF FOR CATALYST FOR HYDRO-CONVERSION OF LCO INVOLVING PARTIAL RING OPENING OF POLY-AROMATICS

(71) Applicant: Indian Oil Corporation Limited, Bandra (East), Mumbai (IN)

(72) Inventors: Ramasubramanian Kanthasamy, Faridabad (IN); Kochappilly Ouseph Xavier, Faridabad (IN); Alex Cheru Pulikottil, Faridabad (IN); Madhusudan Sau, Faridabad (IN); Sanjiv Kumar Mazumdar, Faridabad (IN); Sankara Sri Venkata Ramakumar, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 16/351,088

(22) Filed: Mar. 12, 2019

(65) Prior Publication Data
US 2019/0275503 A1 Sep. 12, 2019

(30) Foreign Application Priority Data
Mar. 12, 2018 (IN) .............................. 201821008923

(51) Int. Cl.
| | | |
|---|---|---|
| *B01J 29/06* | (2006.01) | |
| *B01J 29/08* | (2006.01) | |
| *C10G 47/20* | (2006.01) | |
| *C07C 4/06* | (2006.01) | |
| *B01J 21/04* | (2006.01) | |
| *B01J 31/02* | (2006.01) | |
| *B01J 23/30* | (2006.01) | |
| *B01J 37/08* | (2006.01) | |
| *B01J 37/00* | (2006.01) | |
| *B01J 37/02* | (2006.01) | |
| *C10G 47/18* | (2006.01) | |
| *B01J 29/16* | (2006.01) | |
| *B01J 29/12* | (2006.01) | |
| *B01J 29/14* | (2006.01) | |
| *B01J 35/02* | (2006.01) | |
| *B01J 35/00* | (2006.01) | |

(52) U.S. Cl.
CPC ............. *B01J 29/084* (2013.01); *B01J 21/04* (2013.01); *B01J 23/30* (2013.01); *B01J 29/126* (2013.01); *B01J 29/14* (2013.01); *B01J 29/146* (2013.01); *B01J 29/166* (2013.01); *B01J 31/0235* (2013.01); *B01J 31/0237* (2013.01); *B01J 35/0006* (2013.01); *B01J 35/0046* (2013.01); *B01J 35/026* (2013.01); *B01J 37/0009* (2013.01); *B01J 37/0203* (2013.01); *B01J 37/0213* (2013.01); *B01J 37/08* (2013.01); *C07C 4/06* (2013.01); *C10G 47/18* (2013.01); *C10G 47/20* (2013.01); *B01J 2229/186* (2013.01); *B01J 2229/20* (2013.01); *B01J 2229/30* (2013.01); *B01J 2229/34* (2013.01); *B01J 2229/42* (2013.01); *C07C 2521/12* (2013.01); *C07C 2529/10* (2013.01); *C07C 2529/12* (2013.01); *C07C 2529/14* (2013.01); *C07C 2529/16* (2013.01); *C10G 2300/104* (2013.01)

(58) Field of Classification Search
CPC ........ B01J 29/14; B01J 29/146; B01J 29/126; B01J 29/166; B01J 29/106; B01J 29/084; B01J 2229/186; B01J 2229/42; B01J 2229/20; B01J 2229/30; B01J 2229/34; B01J 31/0237; B01J 31/0218; B01J 31/0235; B01J 31/0202; B01J 31/0271; B01J 35/0006; B01J 35/0046; B01J 35/026; B01J 37/0203; B01J 37/08; B01J 37/0009; B01J 37/0213; C07C 2529/10; C07C 2529/12; C07C 2529/14; C07C 2529/16
USPC ........ 502/60, 62, 63, 64, 66, 69, 74, 79, 85, 502/527.24
See application file for complete search history.

(56) References Cited

U.S. PATENT DOCUMENTS

| | | |
|---|---|---|
| 4,828,675 A | 5/1989 | Sawyer et al. |
| 6,900,365 B2 | 5/2005 | Chen et al. |
| 2010/0116712 A1 | 5/2010 | Dziabala et al. |
| 2012/0085681 A1 | 4/2012 | Abe et al. |

(Continued)

FOREIGN PATENT DOCUMENTS

WO WO2015/128019 A1 9/2015

OTHER PUBLICATIONS

Tang et al., "Design and Synthesis of Metal Sulfide Catalysts Supported on Zeolite Nanofiber Bundles with Unprecedented Hydrodesurfurization Activities", J. Am. Chem. Sod. (2013), 135, pp. 11437-11440.*

(Continued)

*Primary Examiner* — Elizabeth D Wood
(74) *Attorney, Agent, or Firm* — Workman Nydegger

(57) ABSTRACT

The present invention relates to a catalyst composition and a process for preparing thereof, wherein the catalyst composition is specifically active for hydro-conversion of LCO involving mainly the partial ring opening of multi-ring aromatics leading to the production of petrochemical feedstock. The catalyst composition comprises of a carrier comprising ultra-stable Y zeolite and binder alumina, group VIB and VIIIB metal species, and organic additives. The carrier is impregnated with metal solution to form active sites of $WS_2$ slabs of dimensions in the range of 35-45 Å.

7 Claims, 1 Drawing Sheet

(56) References Cited

U.S. PATENT DOCUMENTS

2013/0210611 A1     8/2013   Kim et al.
2013/0292300 A1    11/2013   Yange et al.

OTHER PUBLICATIONS

Becue et al., "Structuring and Catalytic Properties of Zeolite EMT Containing NiMo Sulfide", Journal of Catalysis, 179, pp. 90-99, (1998).*

* cited by examiner

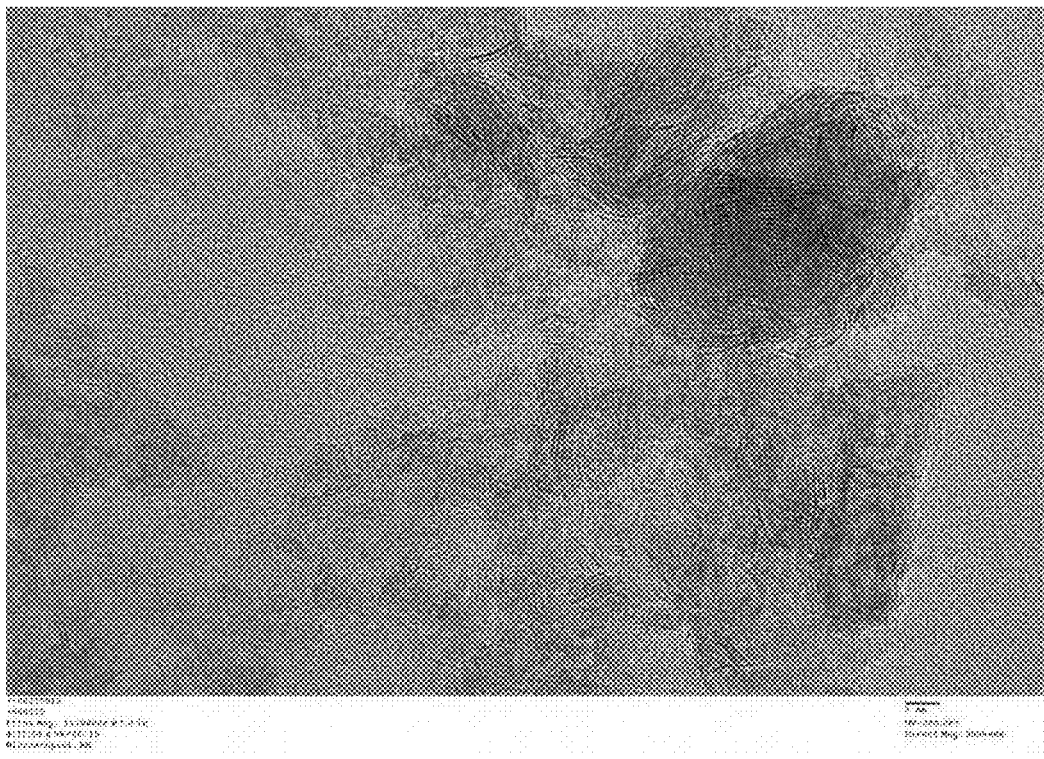
Typical TEM micrograph of catalyst of CAT-A

US 10,843,177 B2

COMPOSITION AND PROCESS THEREOF FOR CATALYST FOR HYDRO-CONVERSION OF LCO INVOLVING PARTIAL RING OPENING OF POLY-AROMATICS

FIELD OF THE INVENTION

The present invention relates to a catalyst composition and a process for preparing thereof, wherein the catalyst composition is specifically active for hydro-conversion of LCO involving mainly the partial ring opening of multi-ring aromatics leading to the production of petrochemical feedstock.

BACKGROUND OF THE INVENTION

Handling of light cycle oil (LCO) is a major concern today for refineries worldwide due to stringent fuel regulations. In General, LCO is used as a diesel blending component. However, the use of LCO is of a limited extent because of its poor cetane properties. Another problem with the use of LCO is presence of sulfur in high quantity in the diesel. In earlier days, refiners had a prospect of using LCO as a blend stock in heavy fuel oil but this provision has been declined recently due to reduction in the requirement of fuel oil worldwide. Therefore, it is imperative to effectively convert LCO to useful products. It is also imperative to effectively convert LCO in order to meet the stringent environmental regulations.

Normally, LCO coming from FCC units contain a major amount of aromatics. In a normal gasoline-oriented operation, the aromatics content of LCO from FCC units can be as high as 80 wt %. Major amount of the aromatics in LCO from FCC units is present as di-aromatics followed by mono-aromatics whereas polycyclic aromatics are present in lower amounts. Hydrocracking at mild conditions may be employed to convert the di and tri-aromatics present in LCO into alkyl benzene. The hydrocracking is done by selectively opening the di and tri aromatics rings and keeping the mono-aromatics ring intact at the same time. The process of selective ring opening requires a suitable catalyst that can operate at mild hydrocracking conditions. For a hydrocracking catalyst to function, the catalyst should contain an optimum amount of both acid sites and hydrogenation function.

US2013/0210611A1 describes a hydrocracking catalyst consisting of beta-zeolite, pseudoboehmite, one or more metals chosen from Groups VIIIB and VIB along with a co-catalyst component for preparation of valuable light aromatic hydrocarbons from polycyclic aromatic hydrocarbons derived from oil and the production of maximum amount of BTX from LCO.

WO2015/128019A1 relates to a process for producing BTX from a mixed hydrocarbon source using catalytic cracking route along with aromatic ring opening and BTX recovery. The invention also relates to a process where the aromatic ring opening and hydrocracking produce LPG. The LPG is further subjected to aromatization to produce BTX. The process uses different catalysts made out of ZSM-5, Zeolite L, zeolite with pore size 5-8 Å for each step of producing LPG, aromatization, ring opening, and BTX.

US2013/0292300A1 describes a hydrocracking process and catalyst composition containing mesostructured zeolitic materials useful for hydrocracking of vacuum gas oil in valuable products. The said catalyst composition comprises of a mesoporous zeolite support material comprising of single-phase crystalline mesostructured zeolite having a structure of faujasite, mordenite or MFI and a mixture of two or more catalytic metals supported on the mesoporous zeolite support along with catalytic nanoparticles.

Another US patent application 2012/0085681A1 describes hydrocracking catalyst composition comprising of titanium incorporated zeolite having a stable catalyst life and showing high cracking activity over a long period for cracking of hydrocarbon oil.

US2010/0116712A1 relates to a process comprising a combination of mild hydrotreating and hydrocracking for converting highly aromatic distillated feeds such as light cycle oil (LCO) into ultra-low sulfur gasoline and diesel fuel. Hydrocracking of LCO to ultra-low sulfur and diesel fuel is carried out by a hydrocracking catalyst comprising of a metal chosen from the Group VIII and VI of periodic table and a beta zeolite support.

U.S. Pat. No. 6,900,365B2 describes a process for converting heavy hydrocarbon feedstream under hydrodealkylation/reforming conditions to high octane gasoline, BTX and other valuable aromatics using a composition comprising of a borosilicate molecular sieves having a pore size greater than 5 Å and a Constraint Index smaller than 1 along with a metal component. The process enables conversion of the heavy hydrocarbon feed to a product comprising benzene, toluene, xylene and ethylbenzene using the composition. The metal component providing the hydrogenation/dehydrogenation function comprises of a Group VIIIA metal along with a promoter from Group VIA metal, Group IIIB-VB metal and a neutralizing component from Group IA and IIA.

Another U.S. Pat. No. 4,828,675 relates to a process for production of ultra-high octane gasoline or high octane gasoline blending components from a sulfur containing feed rich of two-ring aromatic hydrocarbons in the presence of a catalyst. The catalyst comprises of an elemental iron and one or more alkali or alkaline earth metal components, which provides selective hydrogenation and cracking to produce higher octane gasoline or gasoline blending components.

SUMMARY OF THE INVENTION

The primary objective of the present invention relates to a catalyst composition and a process for preparing the same wherein the catalyst composition is specifically active for hydro-conversion of LCO involving mainly the partial ring opening of multi-ring aromatics leading to the production of petrochemical feedstock. The process involves preparation of a catalyst carrier comprising an ultra-stable Y zeolite as a major component and an alumina which acts as binder at optimum ratio, resulting in the formation of desired acidity and acid site distribution tailored for effectively aiding in steps for partial ring opening of poly aromatics moieties.

Another objective of the present invention relates to the process of preparation of catalyst from the catalyst carrier, wherein metals species of group VIB and VIIIB of the periodic table of elements are incorporated into the carrier as oxide as its precursor solutions in the range of 13-20% and 2-6% of total weight of the catalyst, respectively, The present invention also discloses a method of modification of the metal species in the solution phase by reacting an optimum quantity of additives selected from a group of nitrogen and oxygen containing organic compounds with the metal species, wherein the molar ratio of the additive to the Group VI metal component lies in the range of 0.5-5. The method of preparation in accordance to the present invention enables the formation of monomeric metal precursors in solution which then leads to the formation of highly dispersed WS$_2$ slabs active sites on the carrier with a slab dimension in the range of 35-45 Å. Further, the monomeric metal species diffuses into pores of tailored acidic carrier and evenly binds in close association with the acid sites, thereby resulting in features responsible for high conversion of LCO and selective ring opening of aromatics systems.

BRIEF DESCRIPTION OF THE DRAWINGS

FIG. 1 Typical TEM micrograph of catalyst of CAT-A

DESCRIPTION OF THE INVENTION

While the invention is susceptible to various modifications and/or alternative processes and/or compositions, specific embodiment thereof has been shown by way of example in tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The tables and protocols have been represented wherever appropriate by conventional representations, showing only those specific details that are pertinent to understanding the embodiments of the present invention so as not to obscure the disclosure with details that will be readily apparent to those of ordinary skill in the art having benefit of the description herein.

The following description is of exemplary embodiments only and is NOT intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particular and all details set forth herein are used in the context of some embodiments and therefore should NOT be necessarily taken as limiting factors to the attached claims. The attached claims and their legal equivalents can be realized in the context of embodiments other than the ones used as illustrative examples in the description below.

The present invention relates to a catalyst composition and a process for preparing thereof, wherein the catalyst composition is specifically active for hydro-conversion of LCO involving mainly the partial ring opening of multi-ring aromatics leading to the production of petrochemical feedstock.

According to a main embodiment, the present invention provides an active catalyst composition for hydro-conversion of LCO involving the partial ring opening of multi-ring aromatics for the production of petrochemical feedstock. The catalyst composition comprises:
  i. a carrier of the catalyst composition comprising of ultra-stable Y zeolite as a major component, wherein the majority of the acid sites present in the ultra-stable Y zeolite are of weak acid sites;
  ii. binder comprising an alumina, wherein the binder is a minor component of the carrier;
  iii. metals species selected from the group consisting of group VIB and VIIIB metals; and
  iv. additives selected from a group of nitrogen and oxygen containing organic compounds;

wherein the additives are reacted with the metal species to form metal sulfide active sites with slabs of dimension in the range of 35-45 Å required for high hydro-conversion of LCO.

According to a preferred feature of the present invention, the ultra-stable Y zeolites with defined acidity acts as major component of the carrier. The zeolites are synthetic or naturally occurring crystalline aluminosilicate inorganic material characterized by properties such as ion exchange and molecular sieving. Further, the zeolites may be divided in many classes depending on their pore size and architecture. Different zeolites have different pore size, opening, and acidity. The acidity of the zeolite plays an important role in determining the cracking function of the catalyst. The acidity of the zeolite is derived mainly from the strength and number of acid sites. Even if the number of acid sites is small the zeolite can still have high acidity if those acid sites are really strong. Therefore, acidity plays a huge role in choosing a zeolite for a particular application. Conventional refining processes, such as hydrocracking, hydroisomerization, etc. employs a high acidic zeolite or silica alumina with defined pore characteristics for producing fuels, such as gasoline, diesel, and jet fuel. The present invention involves selection of ultra-stable Y zeolite with particular physico-chemical properties and acidity so as to produce petrochemical feedstock by mild hydrocracking of LCO through selective ring opening of aromatics.

According to a feature of the present invention, the ultra-stable Y zeolite is selected with the crystallinity in the range of 80-90%, SiO$_2$/Al$_2$O$_3$ mole ratio in the range of 5-7, and unit cell size (UCS) in the range of 24.5-24.7 Å. The acidity of the zeolite, measured by TPAD, is in the range of 1.2-1.8 mmol NH$_3$/g, preferably in the range of 1.5-1.6 mmol NH$_3$/g, wherein at least 70% of ammonia desorption takes place in the temperature range of 125° C.-375° C. and the remaining in the temperature range of 375° C.-650° C.

According to an embodiment of the present invention, hydrogenation-dehydrogenation function of the catalyst is provided by metal species. In a feature of the present invention, the metal species is selected from group VIB and group VIIIB of the periodic table are used. The group VIB metals are selected from a group consisting of molybdenum, tungsten, and salts and mixtures thereof. The source of tungsten comprises of salts selected from a group consisting from ammonium tungstate, tungsten trioxide, sodium tungstate, tungstic acid, phosphotungstic acid, etc. In another feature of the present invention, the group VIIIB metals are selected from a group consisting of nickel, cobalt, and salts and mixtures thereof. The source of nickel salts is selected from a group consisting of from nickel nitrate, nickel sulfate, nickel carbonate, nickel acetate, nickel chloride, etc.

According to another feature of the present invention, the metal from group VIB is present in the range of 13-20% whereas the metal from group VIIIB is present in the range of 2-6% of the total weight of the catalyst composition. Further, the metal from group VIIIB act as promoters, wherein the group VIIIB promote generation of the active sites in the catalyst. The real catalytic reactions are carried out by the metal from group VIB. The selected metals from group VIB and VIIIB have intrinsic hydrogenation function, which is utilized for desired reactions to take place.

According to yet another feature of the present invention, the catalytic activity can be enhanced by adding suitable additives in optimum proportion which can complex with the metal salts and result in better dispersion of the metal components. The suitable additive is an organic additive selected from a group consisting of a nitrogen and oxygen containing organic compound. The organic additives forms complex with the metal solution and enhances the dispersion of the metals on the surface of the catalyst. Further, the additives that can perform the desired function are selected from a group consisting of ethylenediaminetetraacetic acid, ethanolamine, diethanolamine, triethanolamine, nitrolotriacetic acid, etc.

According to an aspect of the present invention, the organic additive was added in such a way that the molar ratio of the organic additive to the Group VI metal component lies in the range of 0.5-5, which resulted in the better yield of the desired products. Further, the solution of metal species is prepared at a pH in the range of 7-9, which leads to the formation of monomeric metal precursors in solution. This eventually results in the formation of highly dispersed $WS_2$ slabs active sites on the carrier. The active sites formed on the catalyst are nano-sized NiWS phases present in the catalyst. The nano-sized NiWS phases acting as active site are responsible for the catalytic function.

According to another aspect of the present invention, the catalyst formed is sulfided catalyst formed due to the formation of metal sulfide active sites by the reaction of the additives with the metal species.

According to another main embodiment, the present invention also provides a process for preparing a catalyst composition for partial ring opening of multi-ring aromatics in light cycle oil. The process comprises the following steps:
a. mixing ultra-stable Y zeolite with a binder to obtain a mixture;
b. peptizing the mixture obtained in step (a) with a mineral acid to obtain a peptized product;
c. extruding the peptized product obtained in step (b) to obtain an extruded product;
d. drying and calcining the extruded product to obtain a carrier;
e. mixing a group VIB metal with an organic additive to obtain a first metal solution;
f. mixing the first metal solution with a second metal solution to obtain an impregnating solution; wherein the second metal solution comprises of group VIIIB metals; and
g. impregnating the carrier obtained in step (d) with the impregnated solution to obtain an impregnated carrier;
h. drying and calcining the impregnated carrier to obtain a final catalyst.

According to another embodiment, the present invention relates to a process for preparing a catalyst composition where in partial ring opening of multi-ring aromatics present in LCO takes place for obtaining petrochemical feedstock that can produce valuable products such as benzene, toluene and xylene. In particular, the catalyst is capable of performing selective ring opening mechanism efficiently. The catalyst composition obtained is highly active and stable for a long period of operation that can yield very high conversion and selectively result in the production of the value-added petrochemical feedstock as products.

According to a preferred embodiment, the present invention provides preparation of the impregnation solution by preparing solution 1 and solution 2 separately and then mixing them together. The Solution 1 is prepared from a salt of tungsten from sources of ammonium tungstate, tungsten trioxide, sodium tungstate, tungstic acid, phosphotungstic acid, etc along with nitrogen and oxygen and oxygen containing organic additive, such as ethylenediaminetetraacetic acid, ethanolamine, diethanolamine, triethanolamine, nitrolotriacetic acid, etc. The molar ratio of additive to tungsten is 1.5. The Solution 2 is prepared from a salt of nickel like nickel nitrate, nickel sulfate, nickel carbonate, nickel acetate, nickel chloride, etc. The solution 1 and solution 2 are mixed together under vigorous stirring. The pH of the solution was maintained in the range of 7-9 so that nano sized active sites can be created which are desirable for selective ring opening of polyaromatics. Further, the impregnated solution is impregnated in the catalyst carrier to obtain an impregnated carrier. The impregnated carrier is dried and calcined to obtain a final catalyst. Volume of the solutions are maintained in such a way that it is sufficient to fill the pore of the carrier.

According to a feature of the present invention, the impregnation of the catalyst carrier is carried out for a time period of 1 to 4 hrs. In accordance to another feature of the present invention, the impregnated carrier is dried at a temperature in the range of 110 to 140° C. for a time period in the range of 8 to 18 hrs. Further, the impregnated carrier is calcined at a temperature in the range of 500 to 600° C. for a time period in the range of 1 to 6 hrs. In a preferred feature of the present invention, the impregnation is carried out for 2 hrs followed by drying at 120° C. for 16 hrs. The dried catalyst was then calcined at 550° C. for 4 hrs.

According to a detailed embodiment, the present invention relates to a process for preparing a stable and high active catalyst composition comprising of:
(a) a composite carrier in which the major component is an ultra-stable Y zeolite that has an acidity in the range of 1.2-1.8 mmol. equivalent/g as measured through Temperature Programmed Ammonia Desorption (TPAD) wherein at least 70% of the ammonia desorption takes place in temperature range of 125° C.-375° C. and the remaining in the temperature range of 375° C.-650° C. and the minor component is an alumina which acts as binder,
(b) an efficient amounts of metal components selected from metals of the group VIB and VIIIB of the periodic table of elements According to a preferred embodiment, the present invention provides a method for preparing a metal solution wherein an optimum quantity of additive selected from a group of nitrogen and oxygen containing organic compounds where in a molar ratio of the additive to the Group VI metal component lies at a range of 0.5-5 is reacted with the metal species leading to the formation of $WS_2$ active sites with a slab dimension in the range of 35-45 Å.

According to another feature of the present invention, in order to prepare the carrier, the ultra-stable Y zeolite which acts as a major component is first mixed in an optimum ratio with the binder pseudoboehmite alumina to obtain a resultant material. The alumina binder is the minor component. The major component i.e. the ultra-stable Y zeolite is present in the range 50-90% of the total weight of the carrier composition. The resultant material was peptized by mixing with a solution containing mineral acids like nitric acid, hydrochloric acid, formic acid, sulfuric acid, etc. to obtain a mixture. The mineral acids are present in the range of 0.5-3 wt %. The mixture was then extruded in an extruder to obtain an extruded product, followed by drying and calcination. The resultant product is the final carrier in accordance to the present invention.

According to yet another feature of the present invention, the extruded product is dried and calcined at a temperature in the range of 110 to 600° C. for a time period in the range of 4 to 18 hrs.

Fundamental insights on the catalyst structure and active site chemistry were deduced from characterization by TEM spectroscopy. TEM studies provided information on morphological parameters such as number of slabs, slab length, stack height, stacking degree and dispersion of nano-structured $WS_2$ slabs. These morphological parameters such as slab length and stacking degree of the catalyst composition of the current invention which arises because of the presence of the organic additive along with the metal components are responsible for the desired mild hydrocracking and selective ring opening of aromatics present in LCO thereby producing high value petrochemical feedstock.

The catalyst composition of the present invention therefore comprises of an optimum amount of both acid sites and hydrogenation function which is really required for the cracking of LCO to take place at low pressure. This is because hydrocracking at mild conditions may be employed to convert the di and tri-aromatics present in LCO into alkyl benzene and this is done by selectively opening the di and tri aromatics rings and keeping the mono-aromatics ring intact. This process of selective ring opening requires a suitable catalyst that can operate at mild hydrocracking conditions and the catalyst composition as per the current invention provides exactly the same.

EXAMPLES

The present invention is exemplified by following non-limiting examples:

Example-1

Ultra-stable Y zeolite chosen for the catalyst composition of current invention is characterized and the physico-chemical characteristics are provided in the Table 1.

TABLE 1

Characteristics of ultra-stable Y zeolite

| | |
|---|---|
| Crystallinity (%) | 84 |
| $SiO_2/Al_2O_3$ (mole ratio) | 5 |
| Unit Cell Size (UCS), Å | 24.6 |
| BET SA ($m^2/g$) | 612 |
| Single point Pore volume ($cm^3/g$) | 0.38 |
| BJH Desorption average pore diameter (Å) | 58 |
| Pore size distribution | |
| >120 A (%) | 32 |
| 60-120 A (%) | 26 |
| <60 A (%) | 42 |

The ultra-stable Y zeolite contains 58% of pores above 60 Å and has 84% crystallinity.

Acidity measurement by Temperature Programmed Ammonia Desorption (TPAD)

Micromeritics AutoChem II 2920 analyzer was used for measuring the acidity of the zeolite which is used as the major component of the carrier. The acidity (mmol/g) of the ultra-stable Y zeolite was determined by temperature programmed desorption (TPAD) employing ammonia as probe molecule. For acidity measurements, 500-600 mg of sample was first charged into a tubular quartz cell. The sample was maintained at a temperature of 550° C. for 1 h in helium flow and then cooled down to 120° C. This was followed by adsorption of ammonia onto the sample by passing a gas mixture of 10% $NH_3$/He at 20 ml/min for 60 min. After $NH_3$ adsorption, the sample was purged with Helium gas with flow rate of 50 ml/min at 120° C. for 1 h. Subsequently, temperature of the sample was raised to 600° C. at a heating rate of 10° C./min to obtain the total acidity. The amount of ammonia (acidity in mmol $NH_3$I/g) desorbed was determined by inbuilt Autochem peak editing software.

The total acidity of the ultra-stable Y zeolite used as calculated from TPAD measurement is 1.55 mmol $NH_3$/g where in the total acidity of 0.95 mmol $NH_3$/g was observed in the temperature range of 125° C.-375° C. and 0.6 mmol $NH_3$/g the remaining in the temperature range of 375° C.-650° C. The majority of the acid sites present in the ultra-stable Y zeolite are of weak acid sites which account to an extent of at least 70% and the remaining being strong acid sites. Additionally, the highest desorption of ammonia of weak acid sites occurred at a temperature of 240° C. whereas the highest desorption of ammonia of strong acid sites occurred at a temperature of 467° C.

Examples on Tem & Activity of Catalyst after Preparation

Before doing characterization by TEM, the catalyst was sulfided in gas phase using a mixture of $H_2S/H_2$ gas. Typical micrograph of the catalyst showing the slab structure of $WS_2$ phases is shown in FIG. 1. The morphological characteristics of catalyst composition like slab length, slab height, stacking degree, dispersion, etc. were estimated by analyzing more than 100 slabs in the TEM image for each sample. The slab length of CAT-A (as described below example) as calculated from TEM varies from 10-100 Å with an average slab length in the range of 41 Å. The stack height distribution of the active phases also varied in the range of 1-6 with an average stacking degree of 2.5.

Example-2

CAT-A was prepared as per the present invention wherein the catalyst composition comprised of a composite carrier in which the major component is an ultra-stable Y zeolite mentioned in Example-1. First, the ultra-stable Y zeolite was subjected to ball milling for 30 min. This was further ball milled for 20 min with pseudoboehmite alumina being employed as a binder. The resultant material was peptized by mixing with a solution containing 1.5% nitric acid. The mixture was then extruded using ¹⁄₁₆" die in a laboratory extruder. The resultant product was impregnated with a solution consisting of solution 1 and solution 2 along with an organic additive. Solution 1 was prepared from a salt of tungsten from sources of ammonium tungstate along with nitrogen and oxygen and oxygen containing organic additive, "ethanolamine", maintaining a molar ratio of ethanolamine to tungsten at 1.5. Solution 2 was prepared from a salt of nickel like nickel nitrate. The two solutions were mixed together under vigorous stirring. The final composition of the metal solution contains 19% $WO_3$ and 5% NiO. The pH of the solution was maintained in the range of 7-9. Volume of the solution was maintained in such a way that it was sufficient to fill the pore of support. The impregnation was carried out for 2 hrs followed by drying at 120° C. for 16 hrs. The dried catalyst was then calcined at 550° C. for 4 hrs.

Example-3

CAT-B was prepared using the same carrier as mentioned in EXAMPLE-1 except that there was no organic additive added to the metal component comprising of tungsten and nickel as mentioned in EXAMPLE-1. All the other processes like extrusion, metal impregnation, drying, calcinations are the same as EXAMPLE-1.

Example-4

CAT-C was prepared using the same metal component along with organic additive as mentioned in EXAMPLE-1 except that the ultra-stable Y zeolite used in this example contains more number of strong acid sites unlike EXAMPLE-1. The weak acid sites of ultra-stable Y zeolite account to an extent of 50% and the remaining being strong acid sites. All the other processes like extrusion, metal impregnation, drying, calcinations are the same as EXAMPLE-1.

Example-5

Performance Evaluation of Catalysts

The catalysts were evaluated for conversion of LCO to petrochemical feedstock. The feed LCO was characterized before performance evaluation of the catalyst and the feed properties are given in Table 2:

TABLE 2

| LCO Characterization Properties | |
|---|---|
| Specific Gravity at 15° C., IS:1448-P:32 | 0.9380 |
| Total Sulphur by XRF, (ASTM D2622), wt % | 0.92 |
| Total Nitrogen (ASTM D4629), ppmw | 492 |

| Distillation, D-2887, wt % | ° C. |
|---|---|
| IBP | 101 |
| 1 | 113 |
| 5 | 161 |
| 10 | 183 |
| 30 | 228 |
| 50 | 265 |
| 70 | 310 |
| 90 | 363 |
| 95 | 380 |
| 98 | 396 |
| FBP | 419 |

| Mass Spectrometry analysis-22 classes | |
|---|---|
| Hydrocarbon classes | wt % |
| Paraffins | 4.6 |
| Monocycloparaffins | 2.5 |
| Dicycloparaffins | 2.0 |
| Tricycloparaffins | 4.1 |
| Total Saturates | 13.2 |
| Mono-aromatics | |
| Alkylbenzenes | 8.6 |
| Benzocycloparaffins | 7.4 |
| Benzodicycloparaffins | 3.5 |
| Di-aromatics | |
| Naphthalenes | 21.8 |
| Acenaphenes, biphenyls | 10.5 |
| Acenaphthylenes, fluorenes | 13.6 |
| Tri-aromatics | |
| Phenanthrenes | 5.6 |
| Pyrenes | 1.9 |
| PHA | |
| Chrysenes | 0.1 |
| Total Aromatics | 73.0 |
| Thiophenes | 0.3 |
| Benzothiophenes | 9.8 |
| Dibenzothiophenes | 3.7 |
| Naphthobenzothiophenes | 0.1 |
| Sulfur Compounds | 13.9 |

Performance evaluation of the catalysts was carried out using a micro reactor employing 40 cc catalyst volume. The catalyst was first sulfided using dimethyl disulfide (DMDS) at 50 bar hydrogen pressure at 350° C. over a period of 16 hrs. Operating conditions and yield pattern for the catalyst activity studies are given in Table 3. The desired product of petrochemical feedstock for the current invention lies in the boiling range of 65-200° C. as given in Table 3. The product in the boiling range of 65-200° C. was further characterized by Mass Spectrometer and the results are given in Table 4.

TABLE 3

Operating conditions and performance evaluation results

| Operating Parameters | CAT-A | CAT-B | CAT-C |
|---|---|---|---|
| WABT, ° C. | 380 | 380 | 380 |
| LHSV, h$^{-1}$ | 0.67 | 0.67 | 0.67 |
| H$_2$ Partial Pressure, kg/cm$^2$ | 50 | 50 | 50 |
| Product Yield | wt % | wt % | wt % |
| Pet Chem. Feed (65-200° C.) | 50.5 | 37.44 | 36.73 |
| Total Conversion | 85.43 | 45.96 | 49.04 |

TABLE 4

Product properties

| Hydrocarbon classes | Feed | Properties | | |
|---|---|---|---|---|
| | | CAT-A wt % | CAT-B wt % | CAT-C wt % |
| Alkylbenzenes | 8.7 | 46.7 | 31.4 | 25.8 |
| Benzene | — | 4.6 | 3.0 | 1.6 |
| Toluene | — | 19.5 | 12.2 | 10.2 |
| o-xylene | — | 5.9 | 4.2 | 4.4 |
| m/p-xylene | — | 18.8 | 14.8 | 12.0 |

From Table 3, it is clearly evident that the performance of CAT-A is superior to CAT-B and CAT-C. A very high conversion of more than 1.5 times was observed in CAT-A when compared to CAT-B and CAT-C. Further, CAT-A also shows better selectivity towards the production of petrochemical feedstock when compared to CAT-B and CAT-C. Further, it can be seen from Table 4 that CAT-A resulted in the formation of majority of alkylbenzene and petrochemical feedstock products such as Benzene, Tolune, Xylene when compared to CAT-B and CAT-C.

The catalyst prepared according to the present invention shows excellent activity for selectively converting Light cycle oil (LCO) to petrochemical feedstock by mild hydrocracking through selective ring opening reaction. The high activity of the catalyst of the current invention is attributed to the synergy that exists between the distinct acidic sites of the ultra-stable Y zeolite and the metal precursors present along with organic additive in a defined proportion.

The invention claimed is:

1. An active catalyst composition for hydro-conversion of Light Cycle Oil (LCO) involving the partial ring opening of multi-ring aromatics for the production of petrochemical feedstock, comprising:
   i. a carrier of the catalyst composition comprising ultra-stable Y zeolite as a major component, wherein the zeolite contains a majority of weak acid sites present in the ultrastable Y zeolite, wherein the major component is present in the range of greater than 50 wt % to 90 wt % of the carrier;
   ii. binder comprising an alumina, wherein the binder is a minor component of the carrier;

iii. metals species selected from a group consisting of group VIB and VIIIB metals; and
iv. additives selected from a group of nitrogen containing organic compounds and oxygen containing organic compounds;

wherein the additives are reacted with the metal species to form precursors which are converted by sulfidation to slabs of metal sulfide active sites of dimension in the range of 35-45 Å; and wherein the slabs of metal sulfide active sites are required for hydro-conversion of the LCO.

2. The composition as claimed in claim 1, wherein the major component ultrastable Y zeolite has acidity in the range of 1.2-1.8 mmol. equivalent/g as measured through Temperature Programmed Ammonia Desorption (TPAD); and wherein at least 70% of the ammonia desorption takes place in temperature range of 125° C.-375° C. and the remaining in the temperature range of 375° C.-650° C.

3. The composition as claimed in claim 1, wherein components i-iv are combined and results in formation of a carrier to aid in partial ring opening of poly aromatics.

4. The composition as claimed in claim 1, wherein the ultra-stable Y zeolite has crystallinity in the range of 80-90%, $SiO_2/Al_2O_3$ mole ratio in the range of 5-7, unit cell size (UCS) in the range of 24.5-24.7 Å, and acidity in the range of 1.2 —1.8 mmol $NH_3$/g.

5. The composition as claimed in claim 1, wherein the carrier is prepared by peptizing with mineral acids selected from a group consisting of nitric acid, hydrochloric acid, formic acid, sulfuric acid, and mixtures thereof.

6. The composition as claimed in claim 1, wherein the organic additives are selected from a group consisting of ethylenediaminetetraacetic acid, ethanolamine, diethanolamine, triethanolamine, nitrolotriacetic acid, and mixture thereof.

7. The composition as claimed in claim 1, wherein the group VIB metals are selected from a group consisting of molybdenum, tungsten, and salts and mixtures thereof and the group VIIIB metals are selected from a group consisting of nickel, cobalt, and salts and mixtures thereof.

* * * * *